(12) United States Patent
Mazik et al.

(10) Patent No.: US 8,450,318 B2
(45) Date of Patent: May 28, 2013

(54) METHOD TO TREAT INFECTIONS USING ANTI-INFECTIVE AGENTS

(75) Inventors: Monika Mazik, Braunshweig (DE); Jan Balzarini, Heverlee (BE)

(73) Assignees: K.U. Leuven Research and Development, Leuven (BE); Monika Mazik, Braunschweig (DE)

( * ) Notice: Subject to any disclaimer, the term of this patent is extended or adjusted under 35 U.S.C. 154(b) by 739 days.

(21) Appl. No.: 12/531,971

(22) PCT Filed: Mar. 18, 2008

(86) PCT No.: PCT/EP2008/002159
§ 371 (c)(1),
(2), (4) Date: Feb. 18, 2010

(87) PCT Pub. No.: WO2008/113557
PCT Pub. Date: Sep. 25, 2008

(65) Prior Publication Data
US 2011/0136840 A1    Jun. 9, 2011

(30) Foreign Application Priority Data

Mar. 19, 2007 (EP) .................................. 07005562

(51) Int. Cl.
*A01N 43/58* (2006.01)
*A01N 43/40* (2006.01)
*A61K 31/50* (2006.01)
*A61K 31/435* (2006.01)

(52) U.S. Cl.
USPC ........... 514/247; 514/277; 514/315; 514/396; 514/408

(58) Field of Classification Search
USPC .......................... 514/247, 277, 315, 396, 408
See application file for complete search history.

*Primary Examiner* — Yong Chong
(74) *Attorney, Agent, or Firm* — Whitham Curtis Christofferson & Cook, PC

(57) ABSTRACT

Molecules having a spacer unit, linker and recognition unit(s) are used for the treatment of various diseases, disorders and conditions. The compounds are useful in treating infectious diseases and diseases, disorders or conditions related thereto. Further, the methods for treating diseases, disorders or conditions involve recognition and binding of carbohydrate structures.

10 Claims, 7 Drawing Sheets

27 (AB1)

28 (AB6)

29 (Co23)

31 (Ph-Kre)

SC74

SC75

Co12 (6)

Co19

Co28

Co50

Co54

AH16

AH28

AH29

AH30

ABT5

ABT6

H53

K62

METHOD TO TREAT INFECTIONS USING ANTI-INFECTIVE AGENTS

The present invention relates to the use of molecules having a spacer unit, linker and recognition unit(s) for the treatment and prevention of various diseases, disorders and conditions. In particular, the present invention provides compounds useful in preventing or treating infectious diseases and diseases, disorders or conditions related thereto. Further, the present invention relates to methods for preventing or treating diseases, disorders or conditions involving recognition and binding of carbohydrate structures.

BACKGROUND OF THE INVENTION

Infectious diseases are the main cause of morbidity and mortality accounting for a third of the deaths which occur in the world each year. In addition, infectious agents are directly responsible for at least 15% of new cancers, and they also seemed to be involved in the pathophysiology of several chronic diseases (e.g. inflammatory, vascular and degenerative diseases). The main strategies used to prevent infectious diseases are therapy and prophylaxis. Prophylaxis comprises inter alia vaccination or other preventive medicinal treatment of infectious disease focussed on e.g. inhibiting viral replication in infected cells or reducing the number of copies of a virus in cells infected with the virus or other types of microorganisms or preventing infection of the cells, namely the binding and entry into the host cells.

Various strategies and compounds have been described to be useful for preventing or treating infectious diseases. For example, anti-viral properties of 1,6-naphthyridine and 7,8-dihydroisoquinoline derivatives having activity against human cytomegalovirus are described in Bedard Y., et al., Antimicrobial Agents and Chemotherapy, April 2000, pages 929-937. Therein, it is demonstrated that these 1,6-naphthyridine and isoquinoline analogs exhibit a high level of anti human cytomegalovirus activity. It is speculated by Bedard et al., that the naphthyridine derivative were affecting events at the early and late stage of a virus application.

Further, WO 2004/056824 discloses fungicides and fungicidal compositions of naphthyridine derivatives. In addition, WO 2004/083207 discloses antibacterials, namely naphthyridine derivatives, useful in methods of prophylaxis and treatment of bacterial infections. Also, other heterocyclic aromatic compounds are known having anti infective activity.

However, there is still an ongoing need for new compounds being highly specific with low toxicity allowing treating or preventing infectious diseases. In particular, in view of the emergence of drug-resistant strains, it is essential to provide new compounds with anti-infective, e.g. anti-viral activity. Thus, the present invention provides new compounds useful for treating or preventing infectious diseases, in particular, of viral, bacterial parasitic and fungal infections.

The present invention addresses the need for further compounds exhibiting enhanced anti-viral, anti-bacterial, anti-parasitic and anti-fungal activities. That is, the present invention addresses to provide compounds useful in the prevention or treatment of various diseases, disorders and conditions. The invention provides new uses of compounds which specifically interact with carbohydrate molecules being present on the cell surface of host cells.

SUMMARY OF THE INVENTION

The present invention relates to the provision of the use of specific molecules or salts or solvates thereof useful in therapeutic or prophylactic treatment of various diseases, disorders or conditions. In particular, said molecules are useful in prevention or treatment of various diseases, like infectious diseases in particular of viral infections, bacterial infections, parasitic infectious and fungal infections.

The present inventors now found that molecules according to the general formula I are artificial carbohydrates receptors. The acyclic receptors having both neutral and ionic (anionic, cationic) recognition sites show effective binding of carbohydrates, e.g. N-acetylneuraminic acid (Neu5Ac), thus, preventing binding or interaction of foreign invaders with said carbohydrates present on the surface of host cells.

The present invention relates to the use of compounds able to interact with carbohydrates, namely, the present invention relates to new uses of molecules according to general formula I.

Preferably, the molecules have a spacer unit, and at least one, preferably at least two recognition units linked via a linker to the spacer unit.

These molecules are specifically useful for the preparation of pharmaceuticals for preventing or treating infections.

Further, in another embodiment, the present invention relates to methods of treating individuals afflicted with infectious diseases, in particular, with viral infections.

BRIEF DESCRIPTION OF THE DRAWINGS

FIG. 1 shows specific examples of the compounds useful according to the present invention, wherein the recognition unit is a naphthyridine derivative and the spacer unit A is a phenyl derivative.

FIG. 2 provides further examples of compounds useful according to the present invention.

FIG. 3 shows additional compounds tested in the present invention.

FIG. 4 depicts compounds useful according to the present invention.

DETAILED DESCRIPTION OF THE PRESENT INVENTION

Figure 1:
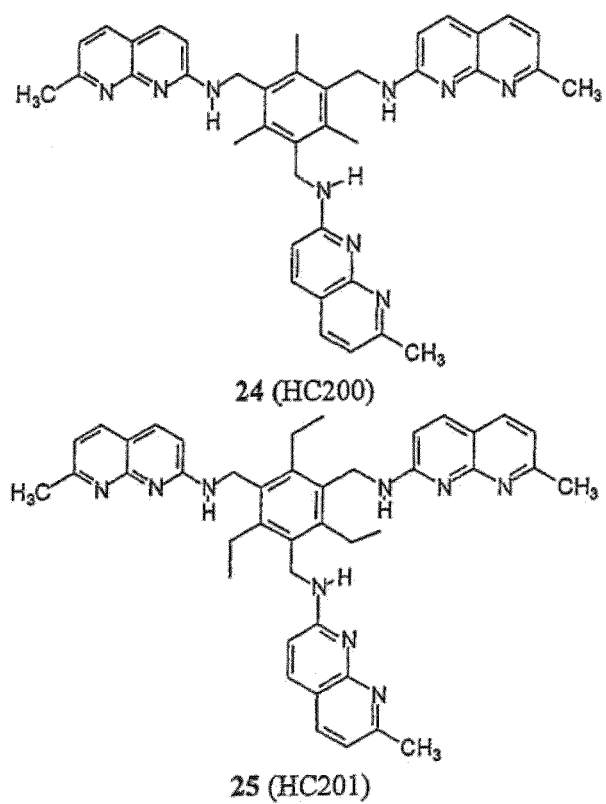
FIG. 1.

The present invention relates to new uses of molecules comprising a spacer unit, a linker and recognition unit(s) of the general formula I $$A\text{-}(\text{-}L\text{-}B)_n \quad (I)$$

wherein the spacer unit A is any one of:
i) a phenyl derivative of the general formula (II):

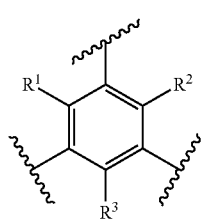

(II)

wherein each $R^1$, $R^2$ and $R^3$ being independently a hydrogen, a $C_1$-$C_6$ alkyl group, a $C_1$-$C_6$ alkoxy group, a hydroxyl group or a halogen;
ii) a biphenyl derivative of the general formula (III);

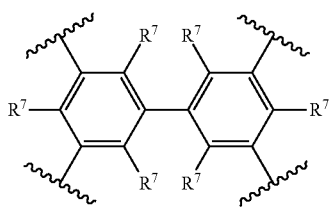

(III)

with each $R^7$ being independently a hydrogen, a $C_1$-$C_6$ alkyl group, a $C_1$-$C_6$ alkoxy group, hydroxyl group or a halogen;

iii) a diphenyl alkane derivative of the general formula (IV):

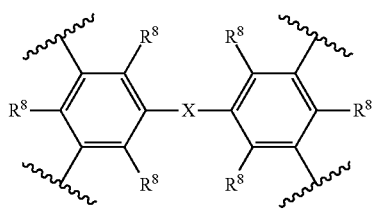

(IV)

with each $R^8$ being independently a hydrogen or a $C_1$-$C_6$ alkyl group, a $C_1$-$C_6$ alkoxy group, hydroxyl group or a halogen; X is a $C_1$-$C_6$ alkylen group, in particular, a methylen group;

iv) a naphthalene derivative of the formula (V)

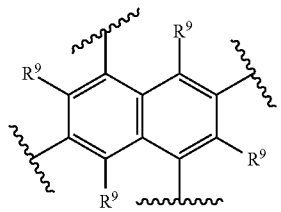

(V)

with each $R^9$ being independently a hydrogen or a $C_1$-$C_6$ alkyl group, a $C_1$-$C_6$ alkoxy group, hydroxyl group or a halogen; the linker L is any one of:

the recognition unit B is any one of:

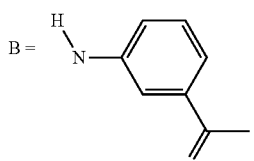

Y = O, NOH

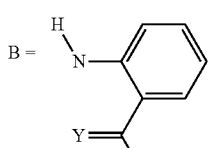

Y = O, NOH

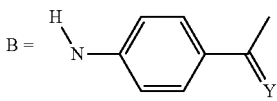

Y = O, NOH

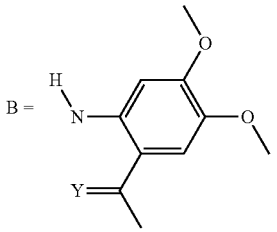

Y = O, NOH

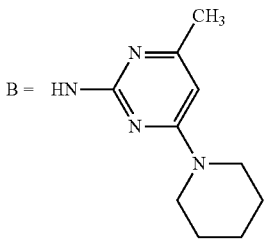

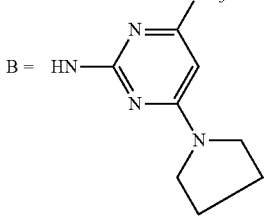
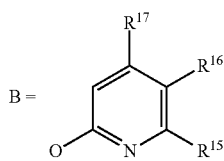

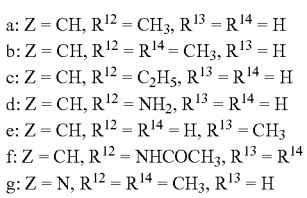

a: Z = CH, $R^{12}$ = $CH_3$, $R^{13}$ = $R^{14}$ = H
b: Z = CH, $R^{12}$ = $R^{14}$ = $CH_3$, $R^{13}$ = H
c: Z = CH, $R^{12}$ = $C_2H_5$, $R^{13}$ = $R^{14}$ = H
d: Z = CH, $R^{12}$ = $NH_2$, $R^{13}$ = $R^{14}$ = H
e: Z = CH, $R^{12}$ = $R^{14}$ = H, $R^{13}$ = $CH_3$
f: Z = CH, $R^{12}$ = $NHCOCH_3$, $R^{13}$ = $R^{14}$ = H
g: Z = N, $R^{12}$ = $R^{14}$ = $CH_3$, $R^{13}$ = H

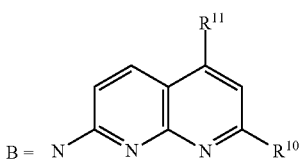

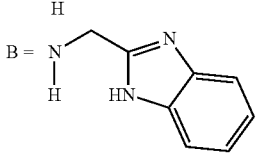

-continued

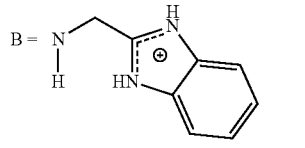
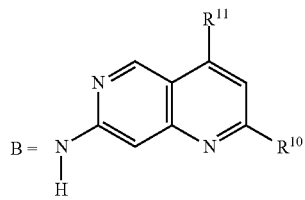
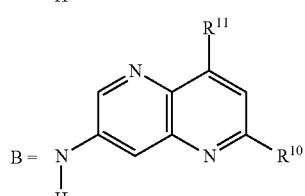
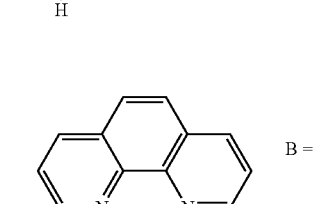
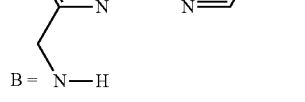
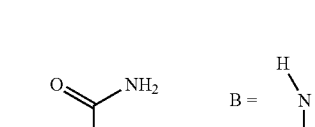
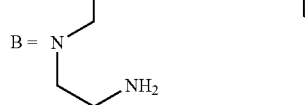
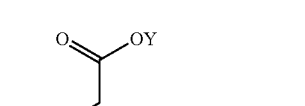
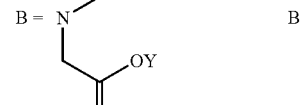
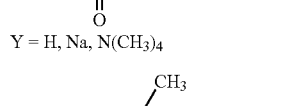
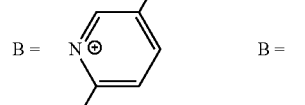

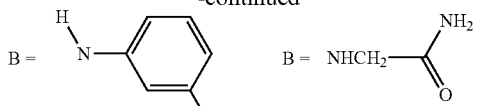
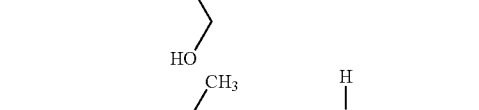
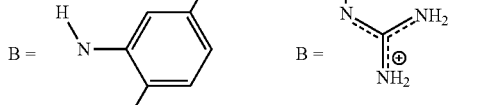
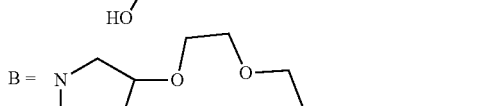
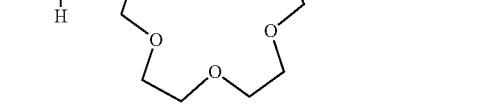
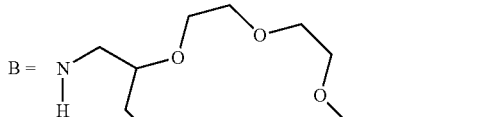
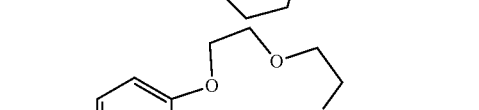
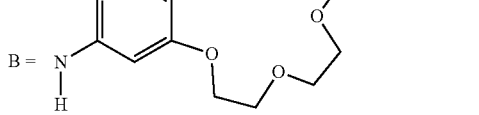
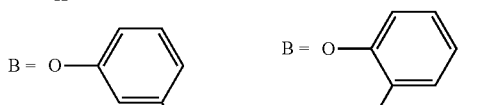
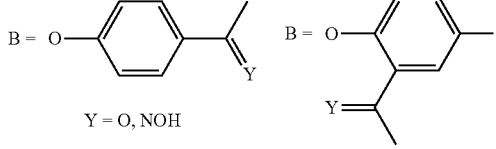
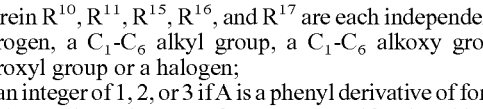
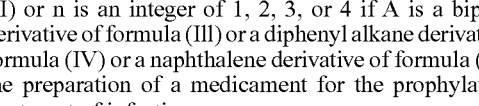

wherein $R^{10}$, $R^{11}$, $R^{15}$, $R^{16}$, and $R^{17}$ are each independently a hydrogen, a $C_1$-$C_6$ alkyl group, a $C_1$-$C_6$ alkoxy group, a hydroxyl group or a halogen;

n is an integer of 1, 2, or 3 if A is a phenyl derivative of formula (II) or n is an integer of 1, 2, 3, or 4 if A is a biphenyl derivative of formula (III) or a diphenyl alkane derivative of formula (IV) or a naphthalene derivative of formula (v) for the preparation of a medicament for the prophylaxis or treatment of infections.

As used herein, the following definitions will apply unless otherwise stated:

A "spacer unit" A as used herein refers to a unit or moiety which is linked to at least one recognition unit B, preferably to at least two recognition units via linker molecules L. The spacer unit may be substituted as indicated herein, namely, the carbon atoms not bound to the linker moiety may be substituted with a residue $R^1$, $R^2$, $R^3$, $R^7$, $R^8$ or $R^9$ each of them being independently a hydrogen, a $C_1$-$C_6$ alkyl group, a $C_1$-$C_6$ alkoxy group, a hydroxyl group or a halogen.

Preferably, at least two recognition units B are bound via a linker L to the spacer unit A whereby said recognition units B may be identical or different.

Figure 2:
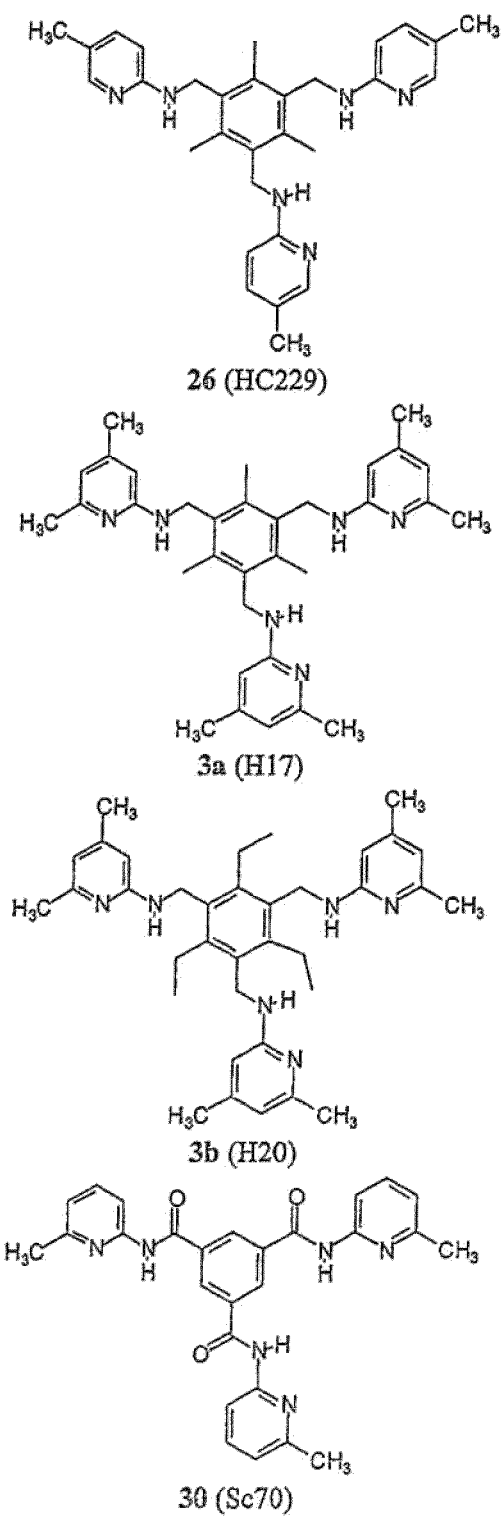
FIG. 2.
Figure 3:
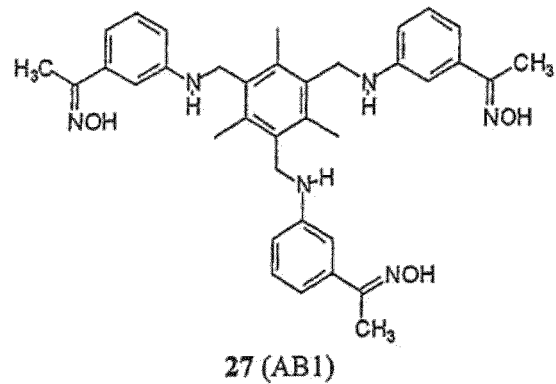
FIG. 3.
Figure 3:
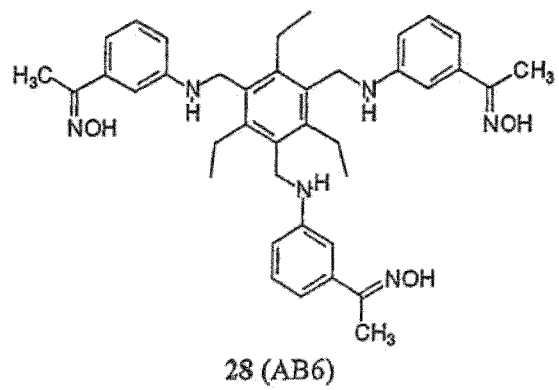
Figure 3:
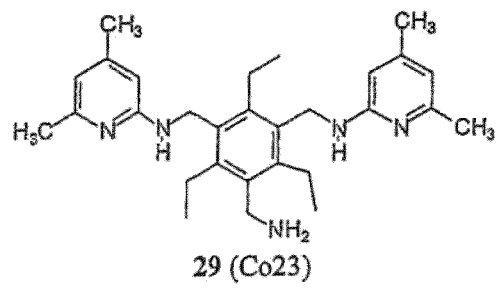
Figure 3:
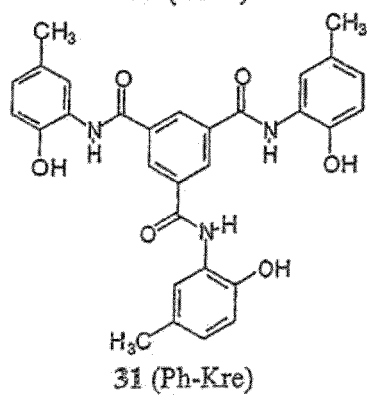

The term "recognition unit" B refers to chemical units or chemical moieties which can interact with carbohydrate moieties. At least one, preferably at least two recognition units are bound via a linker L to a spacer unit A. Embodiments of the recognition units are shown in FIGS. 1 to 3.

As used herein the term "linker" L refers to moieties of $CH_2$—, $CH_2$—CO—, CO—, and O—$CH_2$ which covalently links the spacer unit A with a recognition unit B.

"Therapeutically effective amount" means a quantity of the molecule which is effective in treating the named disorder or condition.

"Pharmaceutically acceptably carrier" is a non-toxic solvent, dispersant, excipient, adjuvant or other material which is mixed with the active ingredient in order to permit the formation of a pharmaceutical composition, i.e. a dosage form capable of administration to the patient. One example of such a carrier is a pharmaceutically acceptable oil typically used for parenteral administration.

As used herein, the term "individual", "subject" or "patient" which is used herein interchangeably refers to an individual, subject or patient in need of the therapy or prophylaxis. The term "subject", "individual" or "patient" as used herein includes but it is not limited to an organism; a mammal including e.g. a human, a non-human primate or other non-human mammals.

As used herein, the term "disease", "disorder", "pathology" and "condition" relates to infectious diseases which may be the cause of other diseases, disorders, pathologies or conditions, e.g. chronic or acute inflammatory processes, autoimmune diseases, cancer, tumors or neurological disorders. In particular, the disease, disorders, pathology and conditions include but are not limited to viral infections, such as hepatitis B virus, hepatitis C virus, Human Immunodeficiency Virus, influenza virus, corona virus infection etc.; bacterial infections such as mycobacteria streptococci and fungal infections such as aspergillus.

A "prophylactic treatment" is a treatment administered to a subject or an individual does not display signs or symptoms of a disease, pathology, or medical disorder or displays only early signs of symptoms of disease, pathology or disorders, such that treatment is administered for the purpose of diminishing, preventing or decreasing the risk of developing the disease, pathology or medical disorder, in particular, the diseases or disorders mentioned above.

A "therapeutic treatment" is a treatment administered to a subject or an individual that display symptoms or signs of pathology, disease or disorder in which treatment is administered to the subject for the purpose of diminishing or eliminating those signs or symptoms of pathology, disease or disorder.

The invention relates to the use of compounds of the formula I in the form of the racemates, racemic-mixtures and pure enantiomers and to their diastereomers and mixtures thereof.

The alkyl residues or alkoxy residues in the substituents, $R^1$, $R^2$, $R^3$, $R^7$, $R^8$, $R^9$, $R^{10}$, $R^{11}$, $R^{15}$, $R^{16}$, and $R^{17}$ may be both straight chain and branched.

If residues or substituents may occur more than once the compounds of the formula I, they may all, independently of another, have the stated meanings and be identical or different.

The term "derivative" refers to compounds derived or obtained from another compound and containing essential elements of the parent substance.

The term halogen refers to fluorine, chlorine, bromine and iodine atom.

The compound according to the present invention can also be administered in combination with further active ingredients. That is, the pharmaceutical compositions may be formulations comprising further active ingredients beside the molecules according to the present invention.

The amount of a compound of formula I necessary to achieve the desired biological effect depends on a number of factors the skilled person is well aware of. The factors include, but not limited to, the specific compounds chosen, the intended use, the mode of administration and the clinical condition of the patient. The pharmaceutical composition of the invention can be produced by one of the known pharmaceutical methods, which essentially consists of mixing the ingredients with pharmacologically acceptable carriers.

As indicated before, all stereoisomers of the compounds of the invention are contemplated, either in the mixture or in pure or substantially pure form. Thus, for example, the compounds of the invention which have one or more centers of chirality and which occur as racemates or as diastereomer mixtures can be fractioned by methods known per se into their optical pure isomers, i.e. enantiomers or diastereomers. The separation of the compounds of the invention can taken place by column separation on chiral or non-chiral phases or by recrystallization from an optionally optical active solvent or with the use of an optically active acid or base or by derivatization with an optically active reagent, such as, for example, an optically active alcohol, and subsequent elimination of the residue.

The substituents $R^1$, $R^2$, and $R^3$ may be independently from each other a hydrogen, a $C_1$-$C_6$ alkyl group, a $C_1$-$C_6$ alkoxy group, a hydroxyl group or a halogen atom. The term "$C_1$-$C_6$" include methyl, ethyl, propyl, isopropyl, butyl, isobutyl, tert-butyl, pentyl and hexyl groups. The term "$C_1$-$C_6$" alkoxy group include methoxy, ethoxy, propoxy, isopropoxy, butoxy, isobutoxy, tert-butoxy, pentoxy and hexoxy group.

Further, the alkyl or alkoxy residues may be substituted, in particular, substitution may be present with a hydroxyl group, halogen, nitro group or $C_1$-$C_6$ alkoxy group.

Residue $R^7$ of the biphenyl derivative of the general formula (III) be independently a hydrogen, a $C_1$-$C_6$ alkyl group, a $C_1$-$C_6$ alkoxy group, hydroxyl group or a halogen. Preferably, $R^7$ is each independently a hydrogen, hydroxyl, methoxy or methyl group. The $C_1$-$C_6$ alkyl group, $C_1$-$C_6$ alkoxy group or halogen are defined as above.

Substituents $R^8$ are each independently a hydrogen, a $C_1$-$C_6$ alkyl group, a $C_1$-$C_6$ alkoxy group, a hydroxyl group or a halogen as defined above; preferably, $R^8$ are each independently a hydrogen or a methyl or methoxy group.

Substituent $R^9$ of the naphthalene derivative of the formula (V) is independently from each occurrence a hydrogen or a $C_1$-$C_6$ alkyl group, a $C_1$-$C_6$ alkoxy group, hydroxyl group or a halogen. Preferably, each $R^9$ is identical. In a preferred embodiment $R^9$ is hydrogen, methyl or methoxy.

Further, X in the general formula IV is a $C_1$-$C_6$ alkylene group. Preferably, X is a methylene or ethylene group.

The linker moiety or linker unit L, which is herein used interchangeably, is any one selected from the group of: —$CH_2$—, —$CH_2$—CO—, —CO—, and O—$CH_2$— whereby in case of more than one recognition unit at a spacer unit the linker may be identical or different. Preferably, the linker moiety is identical within one spacer unit.

The linker unit L is preferably a —$CH_2$—, —$CH_2$—CO— or —CO— group.

As mentioned above, the spacer unit may be substituted with recognition unit(s) B via a linking moiety as defined above.

The recognition unit B is any one of the recognition units shown in the following

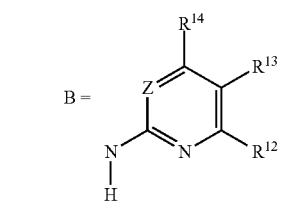

a: Z = CH, $R^{12}$ = $CH_3$, $R^{13}$ = $R^{14}$ = H
b: Z = CH, $R^{12}$ = $R^{14}$ = $CH_3$, $R^{13}$ = H
c: Z = CH, $R^{12}$ = $C_2H_5$, $R^{13}$ = $R^{14}$ = H
d: Z = CH, $R^{12}$ = $NH_2$, $R^{13}$ = $R^{14}$ = H
e: Z = CH, $R^{12}$ = $R^{14}$ = H, $R^{13}$ = $CH_3$
f: Z = CH, $R^{12}$ = $NHCOCH_3$, $R^{13}$ = $R^{14}$ = H
g: Z = N, $R^{12}$ = $R^{14}$ = $CH_3$, $R^{13}$ = H

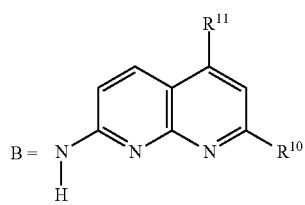

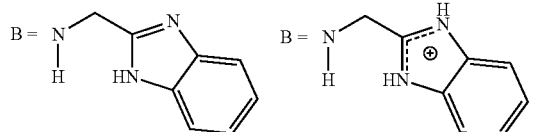

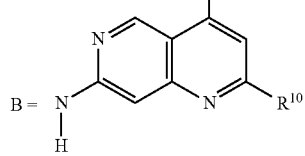

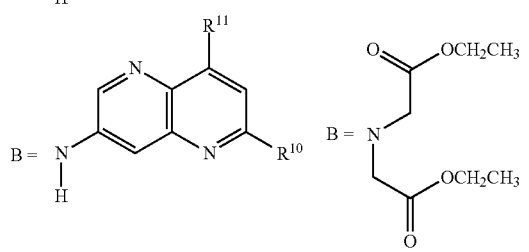

-continued

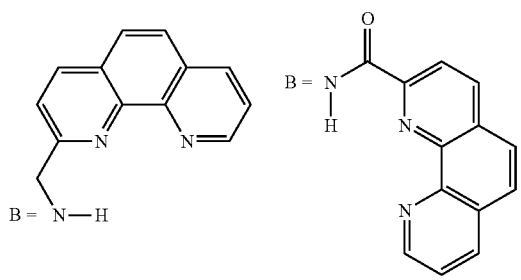

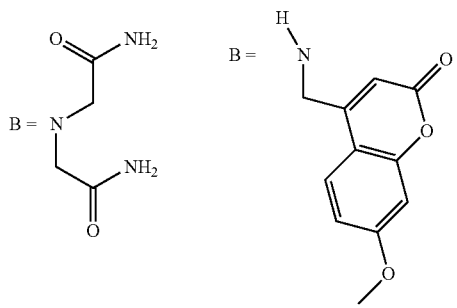

Y = H, Na, N(CH$_3$)$_4$

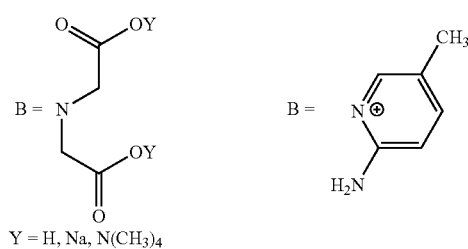

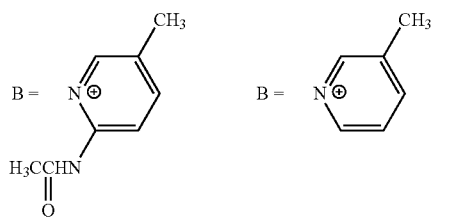

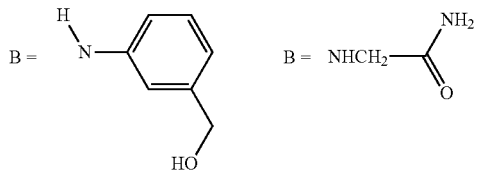

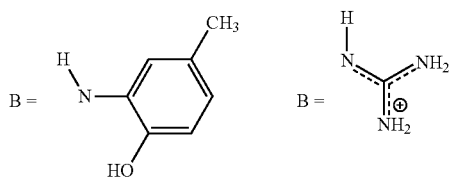

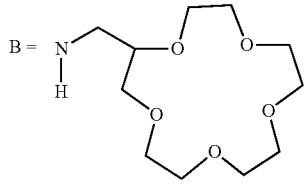

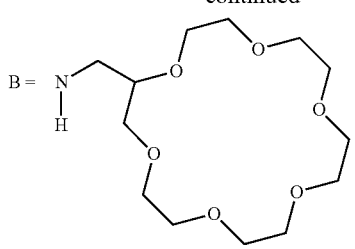
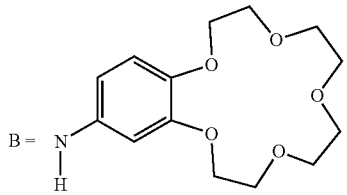
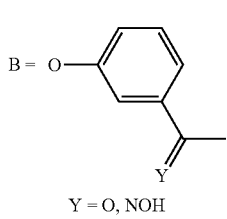
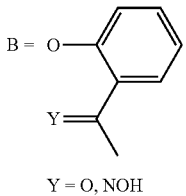
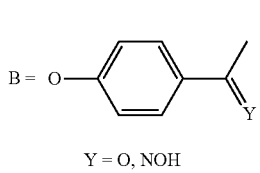
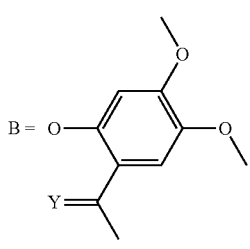
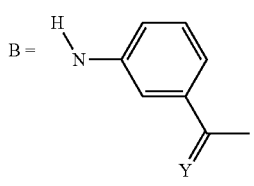
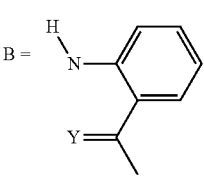
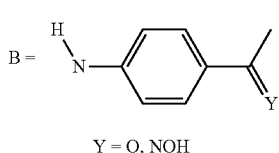
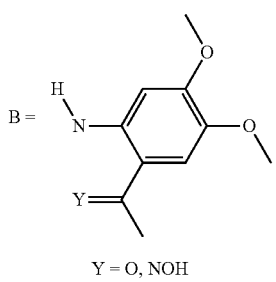

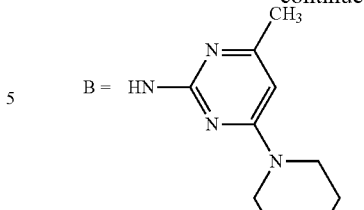
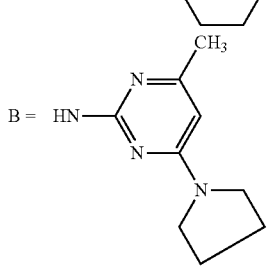
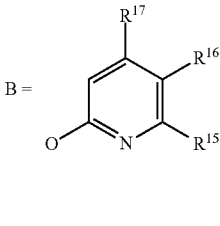

wherein $R^{10}$, $R^{11}$, $R^{15}$, $R^{16}$, and $R^{17}$ are each independently a hydrogen, a $C_1$-$C_6$ alkyl group, a $C_1$-$C_6$ alkoxy group, a hydroxyl group or a halogen.

The recognition units B present at a single spacer moiety may be identical or may be different from each other. Preferably, the recognition units covalently bound to a spacer unit are identical.

At least one recognition unit B is covalently linked with a spacer unit to obtain a compound of the general formula I according to the present invention. That is, n is an integer of 1, 2 or 3 for embodiments wherein the spacer unit is a phenyl moiety of formula II and n is an integer of 1, 2, 3 or 4 in case where the spacer unit is a biphenyl derivative of formula III, a diphenyl alkane derivative of formula IV or a naphthalene derivative of formula V.

Within the present invention, embodiments are contemplated wherein not all possible carbon atoms of the spacer moiety are substituted with a recognition unit B via a linking group as defined above. That is, embodiments are contemplated where n is 1 or 2 in case of a phenyl derivative of formula (II) or n is 1, 2 or 3 for a diphenyl alkane derivative, a naphthalene derivative or a biphenyl derivative. However, embodiments are preferred wherein n is 3 in case of a phenyl derivative of formula II or n is 4 for other spacer moieties than the phenyl derivative.

When the spacer unit A is not fully substituted with recognition units B, said substitutions sites may be substituted with a residue selected from the group of a hydrogen, $C_1$-$C_6$ alkyl group, $C_1$-$C_6$ alkoxy group, hydroxyl group or halogen.

Formulations and Derivatives of Administration

The pharmaceutical composition according to the present invention containing the compounds of the general formula I are typically administered in a formulation that includes one or more pharmaceutically acceptable carriers or excipients. Such pharmaceutical compositions may be prepared in a manner known per se in the art to result in a pharmaceutical that is sufficiently storage stable and is suitable for administration to humans or animals.

Pharmaceutical acceptable carriers or excipients means a carrier or excipient that at the dosages and concentrations employed does not cause any untoward effects in the patients to whom it is administered. Such pharmaceutically acceptable carriers and excipients are well known in the art (e.g. see Remington's Pharmaceutical Sciences, 18th Edition, A. R. Genaro Ed. Mack, Publishing Company (1990), Handbook of Pharmaceutical Excipients, 3rd Edition, A. Kibbe, Ed. Pharmaceutical Press. 2000).

As indicated before, the term "carrier" or "excipient" refers to a carrier, diluent, adjuvant, excipient or vehicle with which the active ingredient is administered. Such pharmaceutical carriers can be sterile liquid, such as water and oils including those of petroleum, animal, vegetable or synthetic origin, such as peanut oil, soybean oil, mineral oil, sesame oil and the like. Water is a preferred carrier when the pharmaceutical composition is administered intravenously. Saline solutions and glycerol solutions can also be employed as liquid carriers, particularly for injectable solutions.

Suitable pharmaceutical excipient include starch, gelatine, malt, rice, fluor, chalk silica gel, sodium stereate, glycerol monostereate, talc, sodium chloride, dried skim milk, glycerol, propylene, glycol, water, ethanol and the like. Pharmaceutical excipients of the sugar type are less preferred due to possible interaction with the active ingredient. The composition if desired, can also contain minor amounts of wetting or emulsifying agents, or pH buffering agents. These compositions can take the forms of solutions, suspensions, emulsion, tablets, pills, capsules, powders, sustained-release formulations and the like. The composition can be formulated as a suppository with traditional binders and carriers such as glycerides. Oral formulations can include standard carriers, such as pharmaceutical grades of starch, sodium stereate, cellulose, magnesium, carbonate etc. Again, carriers based on sugars are less preferred due to possible interaction with the active principle.

The compounds according to the present invention may be also be a component of a pharmaceutical composition provided in a formulation suitable for parentaral administration, in particular, in subcutaneous, intravenous, intradermal or intramuscular administration.

As noted before, the pharmaceutical composition may be adapted for intravenous administration to human beings. Typically, compositions for intravenous administrations are solutions in sterile isotonic aqueous buffer. Where necessary, the composition may also include a solubilizing agent and a local anaesthetic, such as lidocaine to ease pain at the side of injection.

In vitro assays may optionally be employed to help identifying optimal dosage ranges, the precise dose to be employed in the formulation will also depend on the root of administration, and the seriousness of the disease or disorder, and should be decided according to the judgement of the practitioner and each patient circumstance. Effective doses may be extrapolated from dose response curves derived from in vitro animal model test systems. Preferably, the pharmaceutical composition is administered directly or in combination with an adjuvant.

The term "administered" means administration of a therapeutically effective dose of the aforementioned pharmaceutical composition comprising the compounds according to the present invention, salts and solvates thereof as defined herein to an individual.

The administration of the pharmaceutical composition can be done in a variety of ways as discussed above, including, but not limited to orally, subcutaneously, intravenously, intra-aterial, intranodal, intramedullary, intrathecal, intraventricular, intranasal, conjunctival, intrabronchial, transdermally, intrarectally, intraperitonally, intramusculary, intrapulmonary, vaginally, rectally, or intraocularly.

In still another embodiment, the present invention relates to methods of treating individuals suffering from infectious disease, cancer, tumors or other disease or disorders, comprising the step of administering to said individuals an effective amount of a pharmaceutical composition comprising a compound according to formula I or salts or solvates thereof as the active ingredient, and, optionally, a pharmaceutically acceptable carrier. In particular, the method is useful for preventing or treating infectious diseases, like viral, bacterial, parasitic or fungal infections, in particular, hepatitis B, hepatitis C, Human Immunodeficiency Virus, Herpes Virus, influenza or polyoma virus etc.

EXAMPLES

In the following, general synthesis pathways are described allowing to obtain compounds useful according to the present invention. In this context, reference is made to the schemes shown in the following and the reference numbers of the title compounds of each synthesis step are identical with the reference numbers indicated in the schemes.

The examples provided are not intended to limit the claimed subject matter but should illustrate the claimed subject matter further.

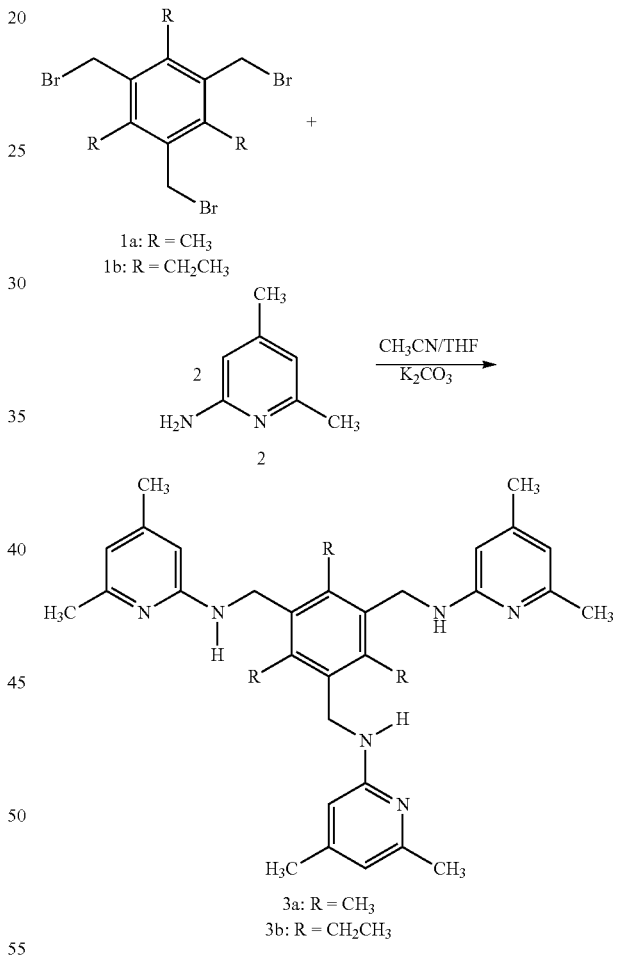

General Procedure for the Synthesis of 3a and 3b:

A mixture of 1,3,5-tris(bromomethyl)-2,4,6-trimethyl- (1a) or -2,4,6-triethyl-benzene (1 b) (3.50 mmol), 2-amino-4,6-dimethylpyridine (2) (2.40 g, 19.67 mmol), and $K_2CO_3$ (1.50 g) in $CH_3CN$ (120 mL) was stirred at room temperature for 24 h and then heated under reflux for 2 h. After filtration of the reaction mixture and evaporation of $CH_3CN$, the obtained powder was suspended in $CHCl_3$. The suspension was filtrated and $CHCl_3$ was removed under reduced pressure. The crude product was crystallized from THF/hexane, ethanol or diethyl ether.

1,3,5-Tris[(4,6-dimethyl-pyridin-2-yl)aminomethyl]-2,4,6-trimethyl-benzene (3a)

Yield 60%. M.p. 193-195° C.; $^1$H NMR (500 MHz, CDCl$_3$): δ=2.21 (s, 9H), 2.33 (s, 9H), 2.38 (s, 9H), 4.11 (t, 3H, J=4.2 Hz), 4.37 (d, 6H, J=4.2 Hz), 6.08 (s, 3H), 6.32 (s, 3H); 2.72 (q, 6H, J=7.6 Hz), 4.09 (t, 3H, J=4.3 Hz), 4.36 (d, 6H, J=4.3 Hz), 6.06 (s, 3H), 6.32 (d, 3H); $^{13}$C NMR (125 MHz, CDCl$_3$): δ=17.0, 21.26, 23.0, 24.3, 40.8, 103.7, 114.0, 133.3, 143.7, 156.8, 158.3; HR-MS calcd for C$_{36}$H$_{48}$N$_6$: 564.3940; found: 564.3931. Anal. Calcd for C$_{36}$H$_{48}$N$_6$: C, 76.55; H, 8.57; N, 14.88. Found: C, 76.38; H, 8.64; N, 14.99.

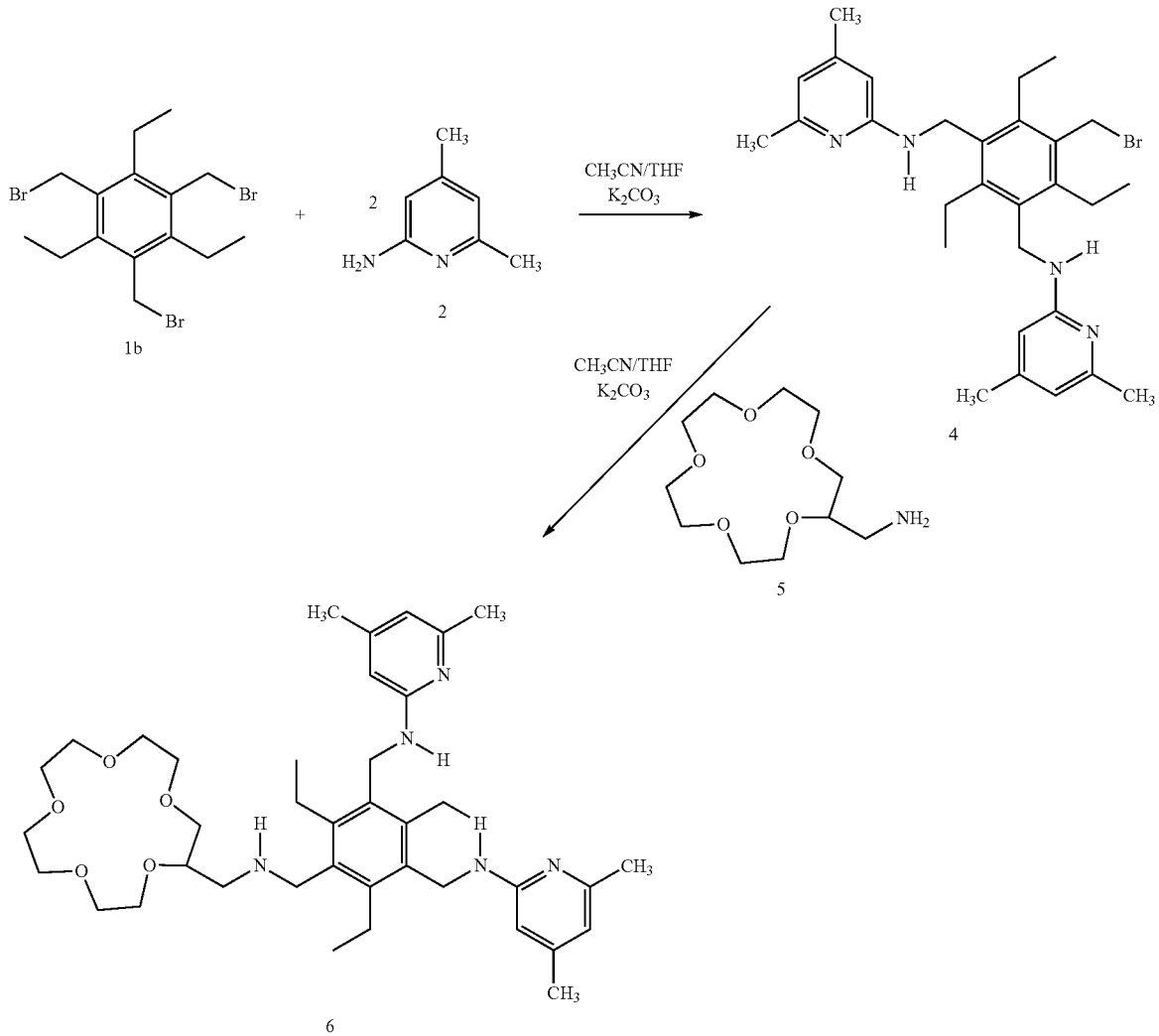

Scheme 2

$^{13}$C NMR (125 MHz, CDCl$_3$); δ=15.9, 21.1, 24.2, 41.8, 103.4, 113.9, 133.7, 136.8, 148.8, 156.7, 158.4; HR-MS calcd for C$_{33}$H$_{42}$N$_6$: 522.3471; found: 522.3477. Anal. Calcd for C$_{33}$H$_{42}$N$_6$: C, 75.82; H, 8.10; N, 16.08. Found: C, 76.01; H, 7.97; N, 15.89.

1,3,5-Tris[(4,6-dimethyl-pyridin-2-yl)aminomethyl]-2,4,6-triethyl-benzene (3b)

Yield 57%. M.p. 183-185° C.; $^1$H NMR (500 MHZ, CDCl$_3$): δ=1.21 (t, 9H, J=7.6 Hz), 2.21 (s, 9H) 2.33 (s, 9H), The synthesis of 6 started from 1,3,5-tris(bromomethyl)-2,4,6-trimethyl-benzene (1b), which was converted into the compound 4 via reaction with two equivalents of 2-amino-4,6-dimethyl-pyridine (2), followed by the reaction with one equivalent of 2-aminomethyl-15-crown-5 (5), as shown in Scheme 2.

Compound 4.

To a mixture of 1,3,5-tris(bromomethyl)-2,4,6-trimethyl-benzene (1b) (3.00 g, 6.80 mmol) and K$_2$CO$_3$ (1.88 g, 13.60 mmol) in CH$_3$CN/THF (1:1 v/v; 40 mL) was added dropwise a CH$_3$CN (10 mL) solution of 2-amino-4,6-dimethyl-pyridine (1.66 g, 13.60 mmol). The mixture was stirred at room temperature for 72 h. After filtration and evaporation of solvents, the crude product was purified by column chromatography (ethyl acetate/toluene, 1:3 v/v). Yield 30%. M.p. 77-78° C. $^1$H-NMR (400 MHz, CDCl$_3$) δ=1.22 (t, 3H, J=7.5 Hz), 1.29 (t, 6H, J=7.5 Hz), 2.24 (s, 6H), 2.36 (s, 6H), 2.73 (q, 2H, J=7.5 Hz), 2.85 (q, 4H, J=7.5 Hz), 4.23 (t, 2H, J=4.2 Hz), 4.37 (d, 4H, J=4.2 Hz), 4.62 (s, 2 H), 6.10 (s, 2 H), 6.35 (s, 2 H). $^{13}$C-NMR (100 MHz, CDCl$_3$) δ=16.4, 16.7, 21.1, 22.8, 23.0, 24.1, 29.6, 40.5, 103.6, 113.9, 131.9, 133.4, 143.8, 144.9, 148.9, 156.5, 158.0. HR-MS calcd for $C_{29}H_{39}BrN_4$ 5232.2353; found: 522.2360. R$_f$ 0.31 (ethyl acetate/toluene, 1:3 v/v).

Compound 6.

To a mixture of compound 4 (262.5 mg, 0.50 mmol) and K$_2$CO$_3$ (69.3 mg, 0.50 mmol) in CH$_3$CN/THF (1:1 v/v; 20 mL) was added dropwise a CH$_3$CN (10 mL) solution of 2-aminomethyl-15-crown-5 (125 mg, 0.50 mmol). The mixture was stirred at room temperature for 48 h. After filtration and evaporation of solvents, the crude product was purified by column chromatography (chloroform/methanol 7:1 v/v). Yield 62%. M.p. 57-58° C. $^1$H-NMR (500 MHz, CDCl$_3$, [1]=0.9 mM) δ=1.23 (t, 9 H, J=7.6 Hz), 2.23 (s, 6 H), 2.35 (s, 6 H), 2.77 (m, 7 H), 3.70 (m, 23 H), 4.25 (br. s, 2 H) 4.36 (d, 4H, J=4.0 Hz), 6.08 (s, 2 H), 6.33 (s, 2 H). $^{13}$C-NMR (100 MHz, CDCl$_3$) δ=16.8 16.9, 21.1, 22.8, 24.1, 40.6, 47.8, 52.1, 70.1, 70.4, 70.5, 70.6, 70.8, 70.9, 71.0, 72.9, 78.7, 103.5, 113.8, 132.7, 142.9, 143.2, 148.8, 156.5, 158.2, 162.7. HR-MS calcd for $C_{40}H_{61}N_5O_5$ 691.4667; found: 691.4671. R$_f$=0.10 (chloroform/methanol, 7:1 v/v).

Scheme 3

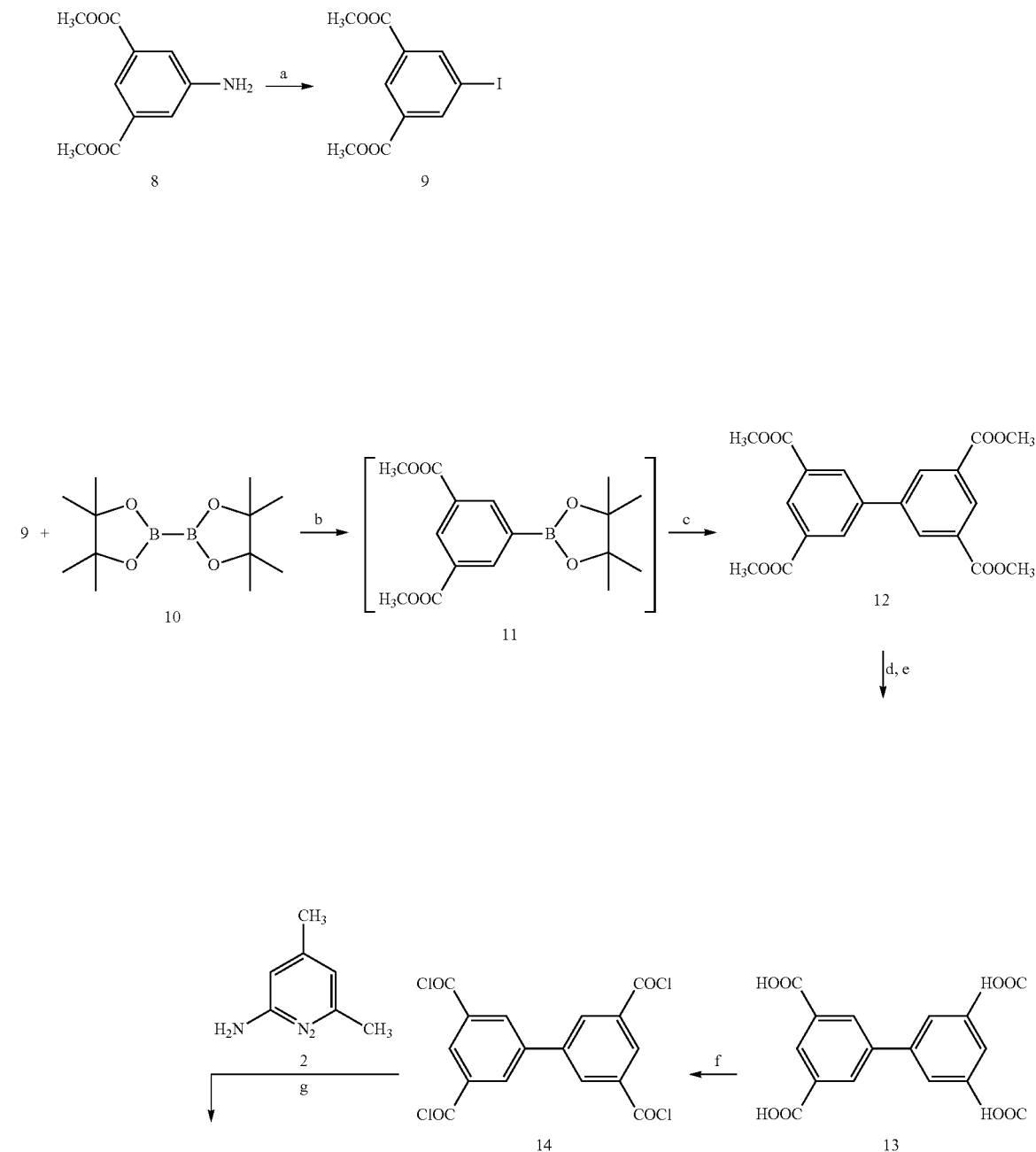

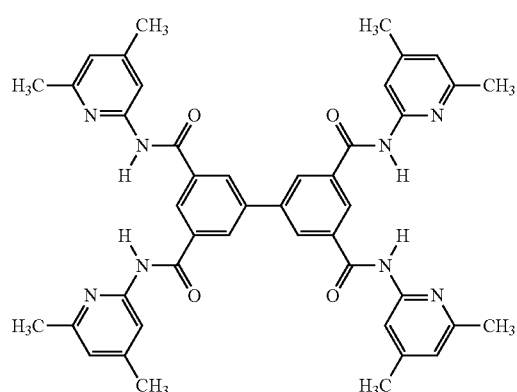

15

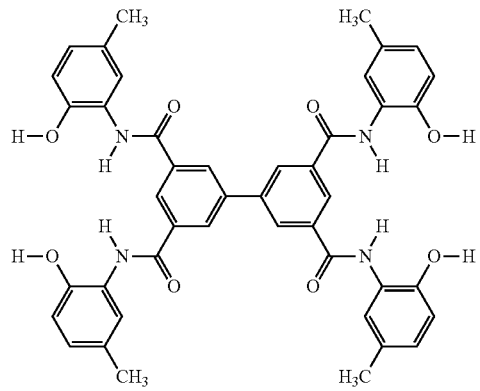

17 a) NaNO$_2$, 20% HCl, KI;
b) PdCl$_2$(dppf), KOAc/DMF, 80° C., 2 h;
c) 2 equiv of 9, PdCl$_2$(dppf), CsF, 80° C., 12 h;
d) 10% NaOH;
e) 50% H$_2$SO$_4$;
f) SOCl$_2$, THF;
g) NEt$_3$, THF;
h) THF.

Dimethyl 5-Iodo-benzene-1,3-dicarboxylate (9)

A solution of sodium nitrite (8.63 g, 0.125 mol) in water (150 mL) was added to a suspension of 5-amino-benzene-1,3-dicarboxylate (8) (26.16 g, 0.125 mol) in 20% HCl (75 mL) at −5° C. Toluene (200 mL) and then a solution of potassium iodide (42.00 g, 0.50 mol) in water (100 mL) was slowly added to the suspension. After the addition, the reaction mixture was stirred for 12 hours and afterwards refluxed for 1 h. The organic layer was separated and washed three times with water, dried with MgSO$_4$, filtered and concentrated in vacuum. The crude product was recrystallized three times from methanol, giving 5 as light-brown crystals. Yield 49%. M.p. 103-104° C. $^1$H-NMR (400 MHz, CDCl$_3$): δ=3.95 (s, 6H), 8.53 (d, 2H, J=1.5 Hz), 8.61 (t, 1H, J=1.5 Hz). $^{13}$C-NMR (100 MHz, CDCl$_3$): δ=52.6, 93.4, 129.8, 132.3, 142.4, 164.7. MS-EI, m/z (%): 320 (88) [M$^+$], 289 (100), 261 (25). R$_f$=0.54 (silica gel, ethylacetate-hexane 3:7 v/v).

3,3',5,5'-Tetrakis(methoxycarbonyl)biphenyl (12)

A mixture of dimethyl 5-iodo-benzene-1,3-dicarboxylate (9) (320 mg, 1.00 mmol), bis(pinacolato)diborane (10) (279 mg, 1.10 mmol), potassium acetate (294 mg, 3.00 mmol), PdCl$_2$(dppf)*(24 mg, 0.03 mmol) and dried DMF (6 mL) was stirred at 80° C. for 2 h. The reaction mixture was cooled to the room temperature. Then, dimethyl 5-iodo-benzene-1,3-dicarboxylate (9) (640 mg, 2.00 mmol), PdCl$_2$(dppf) (24 mg, 0.03) and CsF (456 mg, 3.0 mmol; dissolved in 2.5 mL of water) were added. The mixture was stirred at 80° C. overnight and afterwards extracted for four times with diethylether (4×25 mL). The organic layer was dried with MgSO$_4$ and the solvent was removed in vacuum. The crude product was purified by column chromatography (silica gel, ethylacetate/hexane, 3:7 v/v). Yield 82%. M.p. 214-215° C. $^1$H-NMR (400 MHz, CDCl$_3$): δ=4.00 (s, 12H), 8.51 (d, 4H, J=1.5 Hz), 8.72 (d, 2H, J=1.5 Hz). $^{13}$C-NMR (100 MHz, CDCl$_3$): δ=52.5, 130.2, 131.5, 132.3, 139.9, 165.9. R$_f$=0.50 (silica gel, ethylacetate/hexane, 3:7 v/v). MS-EI, m/z (%): 386 (75) [M$^+$], 355 (100), 327 (15), 194 (10). *[1,1-bis(diphenylphoshino)ferrocene]dichloropalladium(II)].

Biphenyl-3,3',5,5'-tetracarboxylic acid (13)

A mixture of 3,3',5,5'-tetrakis(methoxycarbonyl)biphenyl (12) (0.96 g, 2.5 mmol), THF (40 mL) and NaOH (1.6 g, 40 mmol) dissolved in water (40 mL) was refluxed for 1 h. Then, the organic solvent was removed under reduced pressure, and the aqueous solution was refluxed again for 4 h. The reaction mixture was cooled and acidified with 50% H$_2$SO$_4$. The precipitate was filtrated and dried to obtained 9 as a white powder. Yield 89%. M.p.>350° C. $^1$H-NMR (400 MHz, DMSO-d$_6$): δ=8.44 (d, 4H, J=1.5 Hz), 8.53 (t, 2H, J=1.5 Hz,), 13.48 (bs, 4 H). $^{13}$C-NMR (100 MHz, DMSO-d$_6$): δ=129.5, 131.4, 132.3, 139.2, 166.3. MS-EI, m/z (%): 330 (100) [M$^+$], 313 (40), 285 (15) 240 (5).

N,N',N'',N'''-Tetrakis-[(4,6-dimethylpyridin-2-yl) biphenyl-3,3',5,5'-tetracarboxamide (15)

(a) Synthesis of 14.
A mixture of biphenyl-3,3',5,5'-tetracarboxylic acid (13) (0.30 g, 0.90 mmol) and thionyl chloride (0.53 mL, 7.20 mmol) in THF (20 mL) was heated under reflux for 3 h. The solvent was removed in vacuum. Then, THF (4×20 mL) was added and again the solvent was removed in vacuum. The crude product was used directly for further reaction. (b) Synthesis of 15. A solution of 14 in THF (20 mL) was added dropwise to a solution of 2-amino-4,6-dimethylpyridine (2) (0.47 g, 3.81 mmol) and triethylamine (0.76 mL) in THF (20 mL). After complete addition, the mixture was stirred at room temperature for 48 h. The reaction mixture was treated with water (100 mL), stirred for 15 min, and THF was removed in vacuum. The resulting precipitate was filtered, washed with water, dried, and recrystallized from THF/hexane or chloroform. Yield 76%. M.p. 181-182° C. $^1$H-NMR (500 MHz, CDCl$_3$): δ=2.31 (s, 12 H), 2.37 (s, 12 H), 6.72 (s, 4H), 8.01 (s, 4H,), 8.47 (d, 4H, J=1.8 Hz), 8.53 (t, 2H, J=1.8 Hz), 8.91 (bs, 4H). $^{13}$C-NMR (125 MHz, DMSO-d$_6$): δ=20.9, 23.2, 111.9, 120.4, 127.2, 129.8, 135.1, 139.1, 149.6, 151,4, 156.1, 165.3. HR-MS calcd for C$_{44}$H$_{42}$N$_8$O$_4$ 746.3329; found: 746.3334. R$_f$=0.94 (silica gel, methanol-chloroform 1:7 v/v).

N,N',N'',N'''-Tetrakis-[(2-hydroxy-5-methyl-phenyl) biphenyl-3,3',5,5'-tetracarbox-amide (17)

A solution of 14 (0.61 mmol) in THF (15 mL) was added dropwise to a solution of 2-amino-4-methylphenol (16) 0.672 g (5.46 mmol) in THF (15 mL). After complete addition, the mixture was stirred at room temperature for 48 h. The reaction mixture was filtered, the THF solution was treated with water (20 mL), stirred for 15 min, and THF was removed in vacuum. The resulting precipitate was filtered, washed with water, and dried in vacuum. Yield 77%. M.p. 292-293° C. $^1$H-NMR (400 MHz, DMSO-d$_6$): δ=2.25 (s, 12H), 6.84 (d, 4H, J=8.1 Hz, 4H), 6.89 (dd, 4H, J=8.1/1.7 Hz), 7.46 (d, 4H, J=1.7 Hz), 8.57 (s, 2H), 8.63 (d, 4H, J=1.3 Hz), 9.46 (s, 4H), 9.92 (s, 4H). $^{13}$C-NMR (100 MHz, DMSO-d$_8$): δ=20.21, 115.89, 124.83, 125.02, 125.42, 126.55, 127.49, 129.06, 135.58, 139.29, 147.63, 164.73. HR-MS calcd for C$_{44}$H$_{37}$N$_4$O8[M−H$^+$] 749.2606; found: 749.2610. R$_f$=0.54 (silica gel, methanol-chloroform 1:7 v/v).

Scheme 4

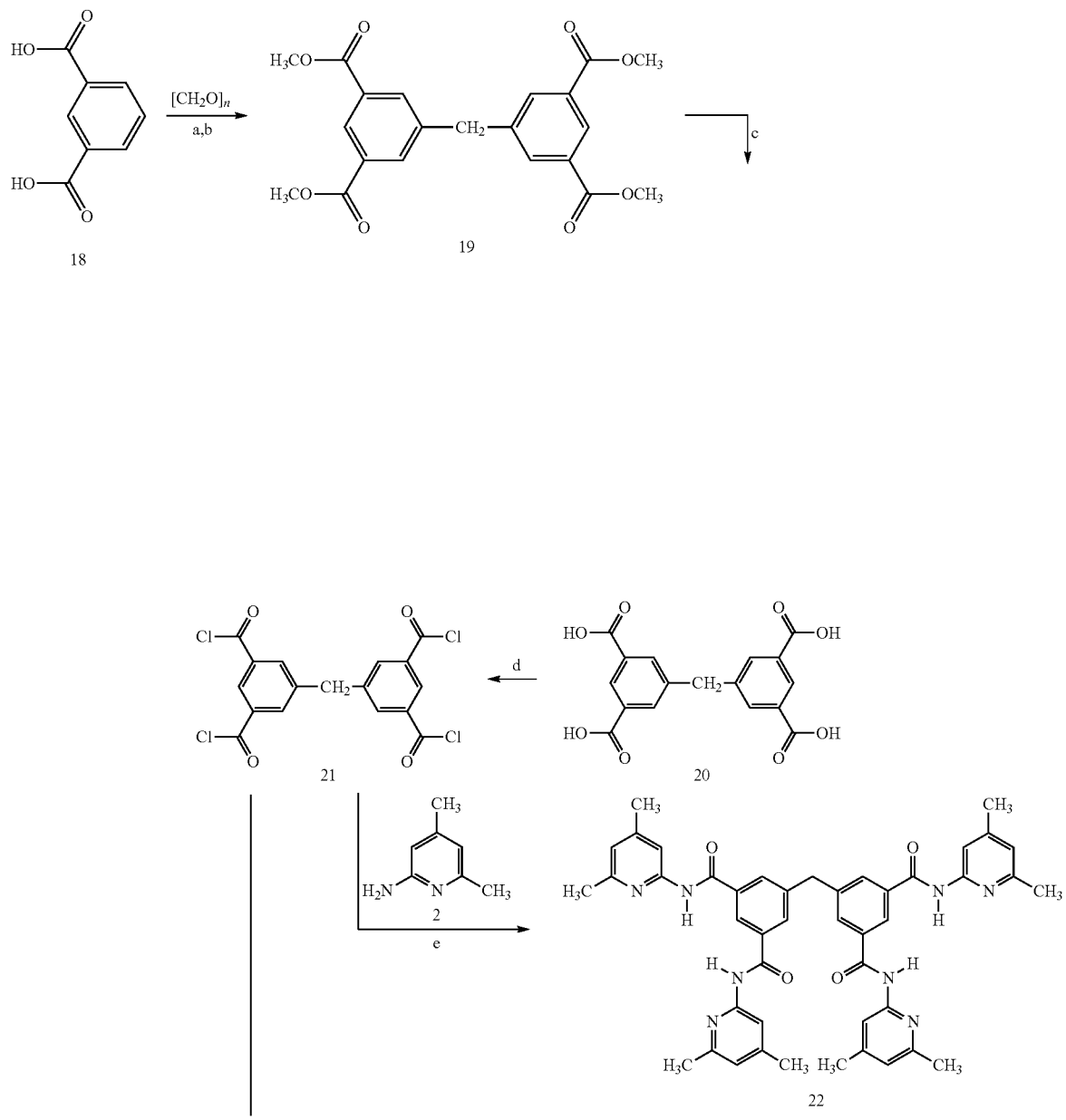

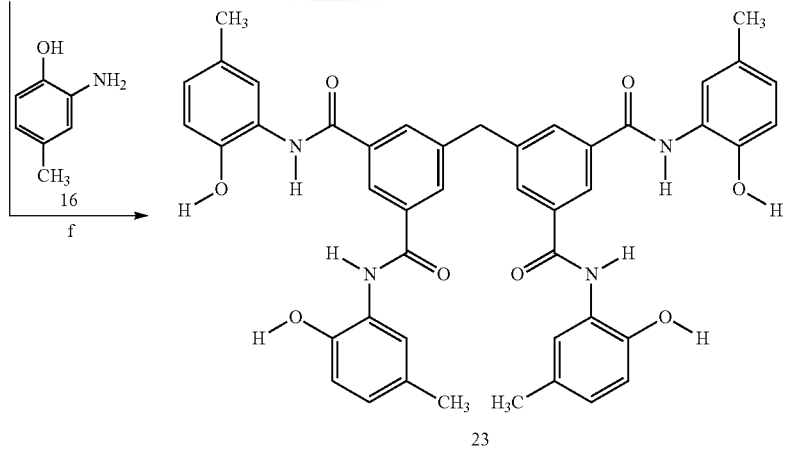

a) 20% Oleum; b) CH₃OH, HCl; c) 10% NaOH; 50% H₂SO₄; d) SOCl₂, THF; e) NEt₃, THF; f) 9 equiv of 16, THF.

3,3',5,5'-Tetrakis(methoxycarbonyl)diphenylmethane (19)

Isophthalic acid (18) (33 g, 0.2 mol) was dissolved in 100 mL of 20% oleum. To the solution, 95% paraformaldehyde (3.1 g, 0.1 mol) was added. The mixture was maintained at 118° C. for 6 hours. After cooling down to room temperature, the mixture was poured onto ice water. The precipitate was filtered, washed with water, and dried in a vacuum. The yellow solid was dissolved in methanol (100 mL), saturated with HCl and refluxed for 30 min. The mixture was cooled to 10° C. and the solid product which appeared was filtered, washed with cold methanol, and dried. To remove last impurities, the solid was recrystallized from benzene and from ethylacetate. Yield 12%. M.p. 197-198° C. $^1$H-NMR (400 MHz, CDCl₃): δ=3.93 (s, 12H), 4.16 (s, 2H), 8.05 (d, 4H, J=1.5 Hz), 8.55 (t, 2H, J=1.5 Hz). $^{13}$C-NMR (100 MHz, CDCl₃): δ=41.1, 52.4, 129.1, 131.1, 134.2, 140.8, 166.1. $R_f$=0.93 (silica gel, methanol/chloroform, 1:7 v/v). MS-EI, m/z (%): 400 (55) [M⁺], 369 (100), 341 (22), 281 (18).

3,3',5,5'-Tetracarboxydiphenylmethane (20)

A mixture of 3,3',5,5'-Tetrakis(methoxycarbonyl)diphenylmethane (19) (1.2 g, 3.0 mmol), THF (50 mL) and NaOH (1.92 g, 48 mmol) dissolved in water (50 mL) was refluxed for 1 h. Then, the organic solvent was removed under reduced pressure, and the aqueous solution was refluxed again for 4 h. The reaction mixture was cooled and acidified with 50% H₂SO₄. The precipitate was filtered, washed with water, and dried. Yield 91%. M.p. 348-350° C. $^1$H-NMR (400 MHz, DMSO-d₆): δ=4.29 (s, 2H), 8.08 (d, 4H, J=1.5 Hz), 8.34 (t, 2H, J=1.5 Hz), 13.26 (s, 4H). $^{13}$C-NMR (100 MHz, DMSO-d₆): δ=39.8, 128.1, 131.5, 133.6, 141.9, 166.5. MS-EI, m/z (%): 344 (55) [M³⁰], 299.26 (100), 179 (12), 165 (20).

N,N',N'',N'''-Tetrakis-[(4,6-dimethylpyridin-2-yl)diphenylmethane-3,3',5,5'-tetracarboxamide (22)

(a) Synthesis of 21.

A mixture of 3,3',5,5'-tetracarboxydiphenylmethane (0.2 g, 0.58 mmol) and thionyl chloride (0.34 mL, 4.65 mmol), in THF (20 mL) was heated under reflux for 3 h. The solvent was removed in vacuum. Then, THF (4×20 mL) was added and again the solvent was removed in vacuum. The crude product was directly used for further reaction.

(b) Synthesis of 22.

A solution of 22 (0.87 mmol) in THF (20 mL) was added dropwise to a solution of 2-amino-4,6-dimethylpyridine (2) (0.63 g, 5.16 mmol) and triethylamine (0.74 mL, 10.15 mmol) in THF (20 mL). After complete addition, the mixture was stirred at room temperature for 48 h. The reaction mixture was treated with water (100 mL), stirred for 15 min, and THF was removed in vacuum. The resulting precipitate was filtered, washed with water, dried, and recrystallized from THF/hexane. Yield 70%. M.p. 181-182° C. $^1$H-NMR (400 MHz, CDCl₃): δ=2.16 (s, 12H) 2.30 (s, 12H), 3.95 (s, 2H), 6.71 (s, 4H), 7.78 (s, 4H), 7.93 (s, 4H), 8.66 (s, 2H), 10.05 (s, 4H). $^{13}$C-NMR (100 MHz, DMSO-d₆): δ=21.0, 23.4, 41.3, 113.1, 120.8, 126.9, 130.7, 134.5, 140.6, 150.1, 150.8, 156.2, 164.7. HR-MS calcd for C₄₅H₄₄N₈O₄ 760.3485; found: 760.3468. $R_f$=0.95 (silica gel, methanol-chloroform 1:7 v/v).

N,N',N'',N'''-Tetrakis-[(2-hydroxy-5-methyl-phenyl)diphenylmethyl-3,3',5,5'-tetracarbox-amide (23)

A solution of 21 (0.58 mmol) in THF (20 mL) was added dropwise to a solution of 2-amino-4-methyl-phenol (0.71 g, 5.85 mmol) in THF (20 mL). After complete addition, the mixture was stirred at room temperature for 48 h. The reaction mixture was treated with water (25 mL), stirred for 15 min and THF was removed in vacuum. The resulting precipitate was filtered, washed with water, dried and dissolved again in small amounts of THF. The solution was purified by column chromatography (silica gel, methanol/chloroform 1:7; v/v). Yield 45%. M.p. 210-211° C. $^1$H-NMR (300 MHz, DMSO-d₆): δ≈2.22 (s, 12H), 4.32 (s, 2H), 6.81 (d, 4H, J=8.1 Hz), 6.86 (dd, 4H, J=8.1/1.7 Hz), 7.45 (d, 4H, J=1.7 Hz, 4H), 8.10 (s, 4H), 8.42 (s, 2H), 9.44 (s, 4H), 9.66 (s, 4H). $^{13}$C-NMR (DMSO-$d_6$): δ=20.2, 39.6, 115.7, 124.5, 125.0, 125.1, 126.3, 127.5, 131.1, 134.9, 141.5, 147.3, 164.7. HR-MS calcd for $C_{46}H_{39}N_4O_8$ [M−H$^+$] 763.2762; found: 763.2767. $R_f$=0.54 (silica gel, methanol-chloroform 1:7 v/v).

Experiments on Anti-Viral and Cytotoxic Activity

Antiretrovirus assays. CEM cells ($4.5 \times 10^5$ cells/ml) were suspended in fresh culture medium and infected with HIV-1 at 100 CCID$_{50}$ per ml of cell suspension in the presence of appropriate dilutions of the test compounds. After 4 to 5 days incubation at 37° C., giant cell formation was recorded microscopically in the CEM cell cultures. The 50% effective concentration (EC$_{50}$) corresponds to the compound concentrations required to prevent syncytium formation by 50% in the virusinfected CEM cell cultures. The 50% cytostatic concentration was defined as the compound concentration required to inhibit CEM cell proliferation by 50%.

In the co-cultivation assays, $5 \times 10^4$ persistently HIV-1 infected HUT-78 cells (designated HUT-78/HIV-1) were mixed with $5 \times 10^4$ Sup-T1 cells, along with appropriate concentrations of the test compounds. After 16 to 20 h, marked syncytium was determined under a microscope.

The results are shown in table 1

TABLE 1

Anti-HIV-1 and anti-HIV-2 activity and cytotoxic properties of various compounds according to the present invention:

| | | EC50 (µg/ml) | | |
|---|---|---|---|---|
| Compound | Structure | HIV-1 | HIV-2 | CC50 (µg/ml) |
| 25 | See FIG. 1 | 1.25 ± 0.35 | >20 | 81.7 ± 26.0 |
| 26 | See FIG. 2 | >4 | >4 | 22.0 ± 8.2 |
| 27 | See FIG. 3 | >4 | >4 | 20.4 ± 11.4 |
| 28 | See FIG. 3 | >4 | >4 | 10.0 ± 0.98 |
| 3a | See FIG. 2 | >0.8 | >0.8 | 2.63 ± 0.08 |
| 3b | See FIG. 2 | >0.8 | >0.8 | 2.87 ± 0.23 |
| 29 | See FIG. 3 | >0.16 | >0.8 | 1.69 ± 0.02 |
| 30 | See FIG. 2 | >20 | >20 | >100 |

TABLE 1a

Figure 4:
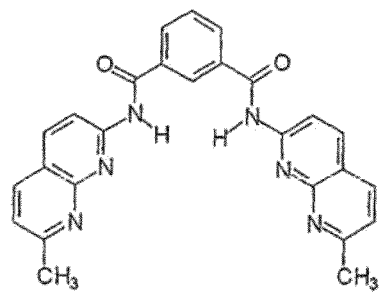
FIG. 4.
Figure 4:
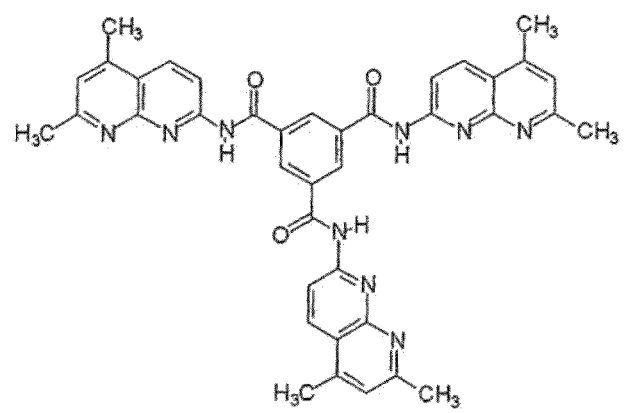
Figure 4:
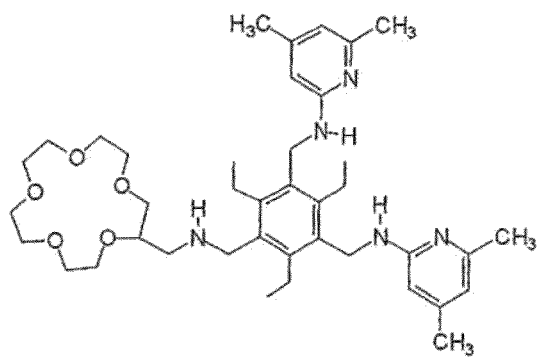
Figure 4:
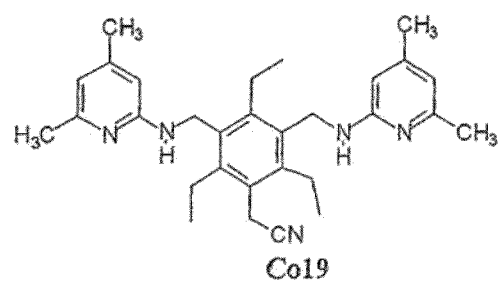
Figure 5:
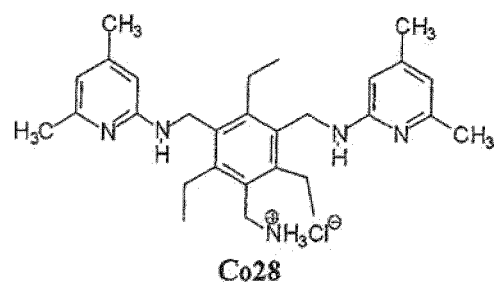
FIGS. 5 to 7 show additional compounds having anti-infective activity as demonstrated in the examples
Figure 5:
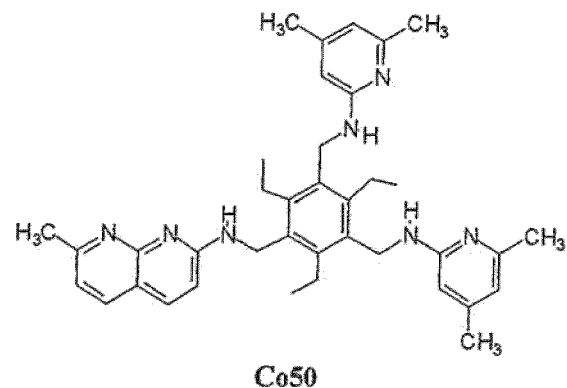
Figure 5:
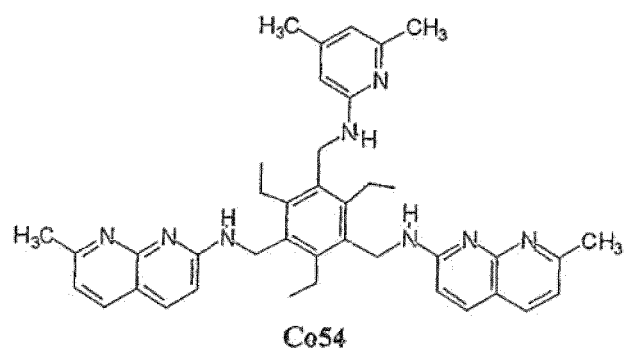
Figure 5:
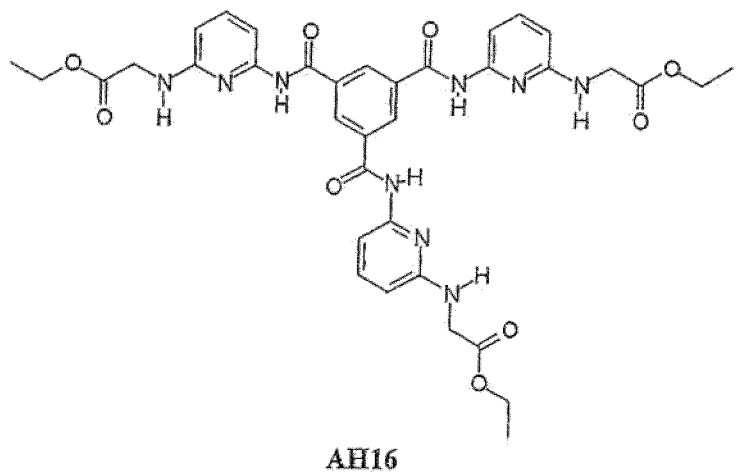
Figure 7:
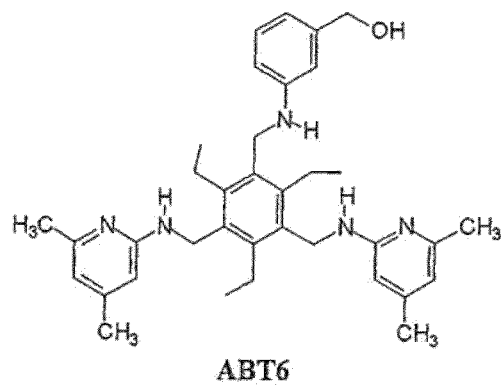
Figure 7:
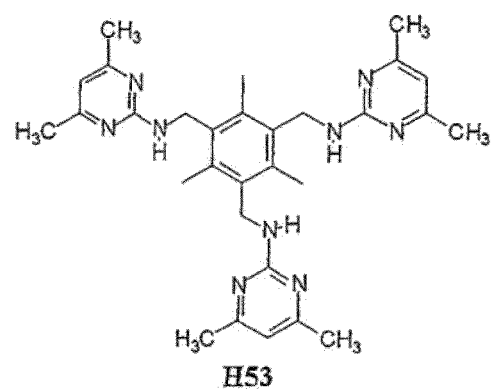
Figure 7:
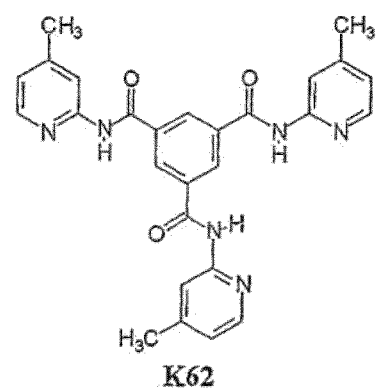

| | | EC50 (µg/ml) | |
|---|---|---|---|
| Compound | Structure | HIV-1 | HIV-2 |
| Co12 | FIG. 4 | 1.35 ± 0.29 | >4 |
| Co50 | FIG. 5 | >2 | >2 |
| Co54 | FIG. 5 | >2 | >2 |
| Co19 | FIG. 4 | >2 | >2 |
| ABT 6 | FIG. 7 | >2 | >2 |

As can be derived from table 1 and table 1a, the compounds according to the present invention display a high anti HIV-1 and/or anti-HIV-2 activity. Compound 24 shown in FIG. 1 gives similar results as compound 25. Further, compound 25 and 30 demonstrates low cytotoxicity The efficiency as anti-virus agent is further demonstrated in systems known in the art, e.g. in CRFK cells for analysing efficiency on feline corona virus and human corona (SARS) virus, see table 2.

TABLE 2

Activity and cytotoxicity on feline and human corona virus

Figure 6:
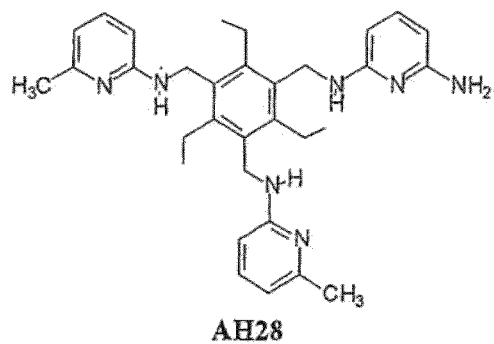
Figure 6:
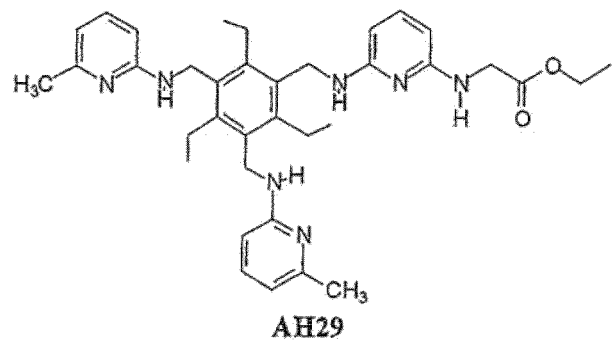
Figure 6:
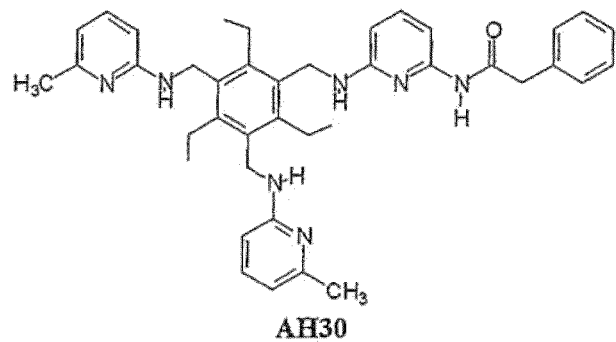
Figure 6:
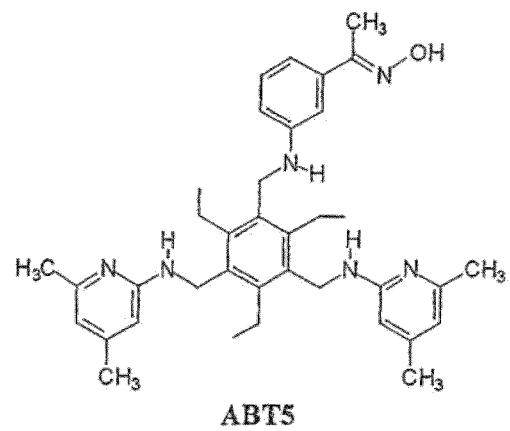

| | | Feline Corona virus | | Human Corona virus | |
|---|---|---|---|---|---|
| Compound | Structure | EC50 (µg/ml) | CC50 (µg/ml) | EC50 (µg/ml) | CC50 (µg/ml) |
| 3b | See FIG. 2 | 1.1 ± 0.6 | 45 ± 21 | 8.6 ± 4.9 | >100 |
| 24 | See FIG. 1 | 42 ± 0 | >100 | 38 ± 1 | >100 |
| 25 | See FIG. 1 | 9.1 ± 0.4 | 92 ± 9 | 20 ± 5 | >100 |
| Co12 | FIG. 4 | 1.4 ± 0.2 | 11 ± 0 | 1.9 ± 0.6 | 13 ± 1.2 |
| 3a | FIG. 2 | 0.8 ± 0.6 | 8.0 ± 4.6 | 1.3 ± 0.2 | 11 ± 1 |
| Sc74 | FIG. 4 | 29.0 ± 4.8 | >100 | — | — |
| AH29 | FIG. 6 | >4 | 13.3 | — | — |
| Co19 | FIG. 4 | >4 | 10.8 | — | — |

As shown above, the compounds according to the present invention are also effective against feline and human Corona virus. It should be noted that when comparing compounds 3a and 3b which differ in residues $R^1$, $R^2$ and $R^3$ only, methyl or ethyl, respectively, differences in the EC50 and, in particular, the CC50 values can be observed.

Furthermore, the compounds have been tested on the various type of viruses identified in the following tables of Influenza virus, Reovirus, Sindbis virus, Coxsackie virus B4, Punta Toro virus, Herpes simplex virus, vaccinia virus, vesicular stomatitis virus and Respirator syncytial virus.

TABLE 3

| | | EC50 | | | | |
|---|---|---|---|---|---|---|
| Compound | Structure (figure) | Para-influenza-3 virus | Reovirus-1 | Sindbis virus | Coxsackie virus B4 | Punta Toro virus |
| Co 23 | 29 (3) | >0.8 | >0.8 | >0.8 | >0.8 | >0.8 |
| Phe-Kresol | 31 (3) | >4 | >4 | >4 | >4 | >4 |
| AB6 | 28 (3) | >4 | >4 | >4 | >4 | >4 |
| HC229 | 26 (2) | >4 | >4 | >4 | >4 | >4 |
| Sc74 | FIG. 4 | >4 | >4 | >4 | >4 | >4 |
| ABT6 | FIG. 7 | >4 | >4 | >4 | >4 | >4 |
| AH16 | FIG. 5 | >4 | >4 | >4 | >4 | >4 |
| Co28 | FIG. 5 | >4 | >4 | >4 | >4 | >4 |
| Brivudin (µM) | | >250 | >250 | >250 | >250 | >250 |
| (S)-DHPA (µM) | | 250 | 250 | >250 | >250 | >250 |
| Ribavirin (µM) | | 250 | 150 | 250 | >250 | 150 |

TABLE 4

| compound | Structure (figure) | EC50 | | | | |
|---|---|---|---|---|---|---|
| | | Herpes simplex virus-1 (KOS) | Herpes simples virus-2 (G) | Vaccinia virus | Vesicular stomatitis virus | Herpes simplex virus-1 TK KOS-ACV$^r$ |
| Co23 | 29 (3) | >0.8 | >0.8 | >0.8 | >0.8 | >0.8 |
| Phe-Kresol | 31 (3) | >4 | >4 | >4 | >4 | >4 |
| AB6 | 28 (3) | 4 | >4 | >4 | >4 | 4 |
| Sc75 | FIG. 4 | >0.8 | >0.8 | >0.8 | >0.8 | >0.8 |
| HC201 *HCl | 25 (1) | >20 | >20 | 0.7 +/− 0.3 | >20 | >20 |
| ABT6 | FIG. 7 | >4 | >4 | >4 | >4 | >4 |
| AH28 | FIG. 6 | >4 | >4 | >4 | >4 | >4 |
| H17 | 3a (2) | >3.2 | >3.2 | >3.2 | >3.2 | >3.2 |
| H20 | 3b (2) | >3.2 | >3.2 | >3.2 | >3.2 | >3.2 |
| H53 | FIG. 7 | >16 | >16 | >16 | >16 | >16 |
| K62 | FIG. 7 | >3.2 | >3.2 | >3.2 | >3.2 | >3.2 |
| HC200 | 24 (1) | >20 | >20 | 1.2 +/− 0.5 | >20 | >20 |
| Brivudin (μM) | | 0.016 | 10 | 2 | >250 | 50 |
| Ribavirin (μM) | | 50 | 150 | 150 | >250 | 150 |
| Acyclovir (μM) | | 0.4 | 0.08 | >250 | >250 | 150 |
| Ganciclovir(μM) | | 0.0064 | 0.032 | 100 | >150 | 12 |

TABLE 5

| | EC50 (μg/ml)$^b$ | | | | | |
|---|---|---|---|---|---|---|
| | Influenza A H1N1 subtype | | Influenza A H3N2 subtype | | Influenza B | |
| compound (figure) | visual CPE score | MTS | visual CPE score | MTS | visual CPE score | MTS |
| Co 23 (3) | >0.8 | >0.8 | >0.8 | >0.8 | >0.8 | >0.8 |
| Phe-Kresol (3) | >0.8 | >0.8 | >0.8 | >0.8 | >0.8 | >0.8 |
| Sc74 (4) | 15.1 +/− 7.0 | 9.6 | 14.5 +/− 7.8 | 12.5 | 10.9 +/− 1.1 | 9.9 |
| Sc75 (4) | >4 | >4 | >4 | >4 | >4 | >4 |
| HC201*HCl (1) | >4 | >4 | >4 | >4 | >4 | >4 |
| ABT5 (6) | >4 | >4 | >4 | >4 | >4 | >4 |
| AH30 (6) | >4 | >4 | >4 | >4 | >4 | >4 |
| Co28 (5) | >0.8 | >0.8 | >0.8 | >0.8 | >0.8 | >0.8 |
| Oseltamivir caboxylate (μM) | 0.004 | 0.003 | 1.8 | 1.6 | 4.0 | 2.6 |
| Ribavirin (μM) | 8.9 | 9.0 | 8.9 | 8.9 | 8.9 | 8.9 |
| Amantadin (μM) | 58.5 | 59.3 | 4.0 | 1.6 | >100 | >100 |
| Rimantadin (μM) | 8.9 | 9.9 | 2.1 | 0.9 | >100 | >100 |

50% Effective concentration, or concentration producing 50% inhibition of virus-induced cytopathic effect, as determined by visual scoring of the CPE, or by measuring the cell viability with the colorimetric formazan-based MTS assay.

MDCK cells (Madin Darby canine kidney cells) have been used for the experiments shown in table 5 using standard procedures known in the art.

The invention claimed is:
1. A method of treating a viral infection from any of lentiviruses, hepatitis B viruses (HBV), Coronaviruses, Flaviviruses, Influenza viruses, Respiratory Syncytial Viruses (RSV), and Parainfluenza viruses in a patient in need thereof, comprising the step of administering to said patient, molecules comprising a spacer unit, linker and recognition unit(s) of the general formula (I)

$$A\text{-}(\text{-}L\text{-}B)_n \qquad (I)$$

wherein the spacer unit A is a phenyl derivative of the general formula (II):

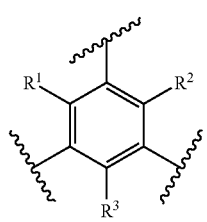

(II)

wherein $R^1$, $R^2$ and $R^3$ being independently a hydrogen, a $C_1$-$C_6$ alkyl group, a $C_1$-$C_6$ alkoxy group, a hydroxyl group or a halogen;
wherein the linker L is any one of:
—$CH_2$—;
—$CH_2$—CO—;
—CO—;
—O—$CH_2$—;

wherein the recognition unit B is any one of:

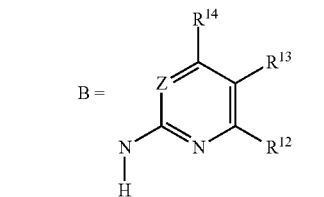

a: Z = CH, $R^{12}$ = CH$_3$, $R^{13}$ = $R^{14}$ = H
b: Z = CH, $R^{12}$ = $R^{14}$ = CH$_3$, $R^{13}$ = H
c: Z = CH, $R^{12}$ = C$_2$H$_5$, $R^{13}$ = $R^{14}$ = H
d: Z = CH, $R^{12}$ = NH$_2$, $R^{13}$ = $R^{14}$ = H
e: Z = CH, $R^{12}$ = $R^{14}$ = H, $R^{13}$ = CH$_3$
f: Z = CH, $R^{12}$ = NHCOCH$_3$, $R^{13}$ = $R^{14}$ = H
g: Z = N, $R^{12}$ = $R^{14}$ = CH$_3$, $R^{13}$ = H

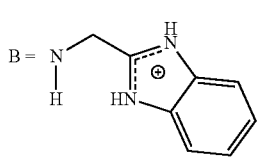

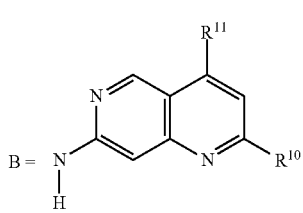

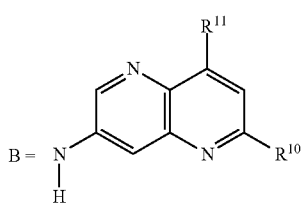

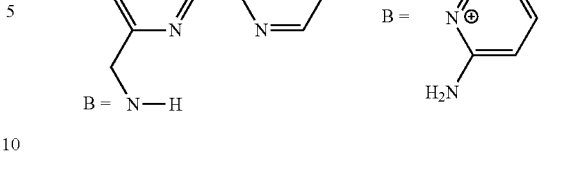

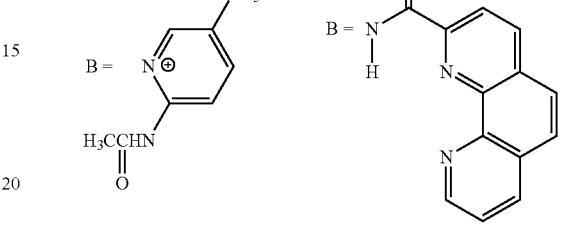

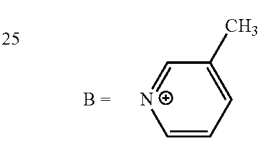

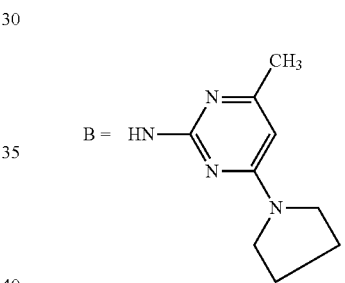

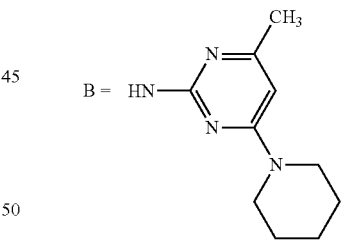

wherein $R^{10}$, $R^{11}$, $R^{15}$, $R_{16}$, and $R^{17}$ are each independently a hydrogen, a C$_1$-C$_6$ alkyl group, a C$_1$-C$_6$ alkoxy group, a hydroxyl group or a halogen; and n is an integer of 1, 2, or 3.

2. The method according to claim 1, wherein the viral infection is an infection with lentiviruses selected from the group consisting of HIV and FIV.

3. The method according to claim 1, wherein each $R^1$, $R^2$ and $R^3$ are independently an alkyl group selected from the group of methyl, ethyl, propyl, or butyl.

4. The method according to claim 3, wherein $R^1$, $R^2$ and $R^3$ are independently a methyl or ethyl group.

5. The method according to claim 1, wherein n is 3.

6. The method according to claim 1, wherein n is 1 or 2.

7. The method according to claim 1, wherein the molecule is
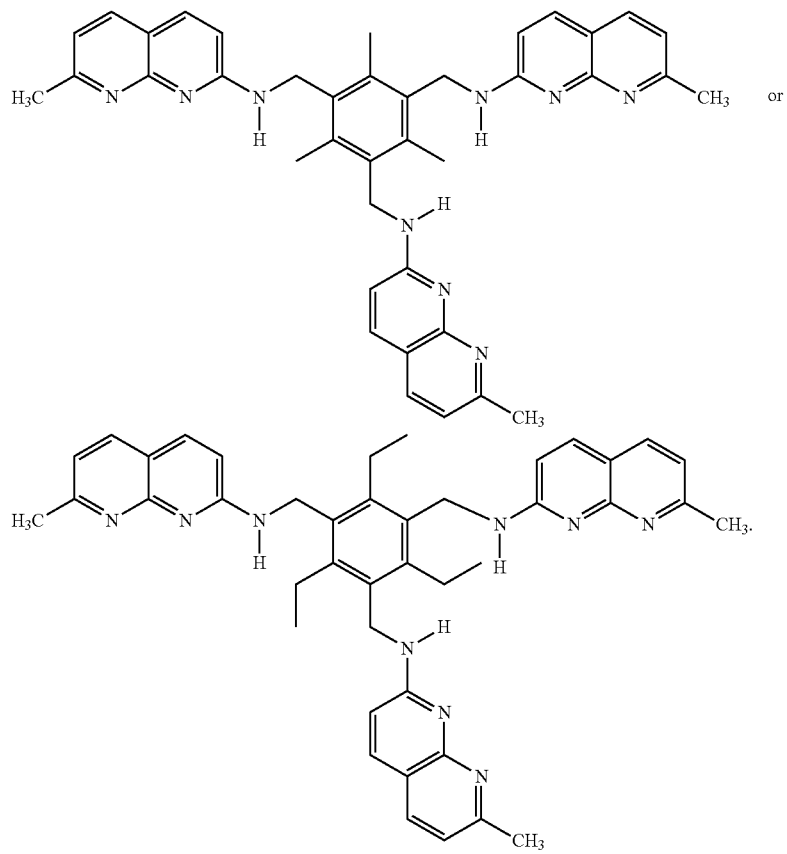
8. The method according to claim 1, wherein the molecule is present as a salt or solvate.
9. The method according to claim 8, wherein the molecules are halogen salts.
10. The method according to claim 1, wherein said molecules are administered in a pharmaceutically acceptable carrier.
* * * * *